(12) United States Patent
Gruionu et al.

(10) Patent No.: US 11,395,708 B2
(45) Date of Patent: Jul. 26, 2022

(54) SYSTEMS AND METHODS FOR AUTOMATIC GUIDANCE OF MEDICAL CATHETERS AND ENDOSCOPES

(71) Applicant: Gabriel Gruionu, Arlington, MA (US)

(72) Inventors: Lucian Gheorghe Gruionu, Craiova (RO); Gabriel Gruionu, Arlington, MA (US)

(*) Notice: Subject to any disclaimer, the term of this patent is extended or adjusted under 35 U.S.C. 154(b) by 528 days.

(21) Appl. No.: 16/442,490

(22) Filed: Jun. 15, 2019

(65) Prior Publication Data

US 2019/0388164 A1     Dec. 26, 2019

Related U.S. Application Data

(60) Provisional application No. 62/687,746, filed on Jun. 20, 2018.

(51) Int. Cl.
*A61B 5/05* (2021.01)
*A61B 34/30* (2016.01)
*A61B 34/20* (2016.01)
*A61M 25/01* (2006.01)
*A61B 34/00* (2016.01)
*A61B 18/00* (2006.01)
(Continued)

(52) U.S. Cl.
CPC .............. *A61B 34/30* (2016.02); *A61B 34/20* (2016.02); *A61M 25/0113* (2013.01); *A61B 18/1492* (2013.01); *A61B 34/25* (2016.02); *A61B 34/70* (2016.02); *A61B 2017/00477* (2013.01); *A61B 2018/00351* (2013.01); *A61B 2018/00577* (2013.01); *A61B 2034/2055* (2016.02); *A61B 2034/301* (2016.02); *A61B 2034/305* (2016.02)

(58) Field of Classification Search
IPC ......... A61B 34/20,34/30, 34/25, 34/70, 34/305, 34/301, 34/2055
See application file for complete search history.

(56) References Cited

U.S. PATENT DOCUMENTS 7,214,230 B2   5/2007   Brock
8,989,528 B2   3/2015   Udd
(Continued)

FOREIGN PATENT DOCUMENTS

CN         101933837       1/2011
WO     WO/2007/005367     1/2007

*Primary Examiner* — Joel F Brutus
(74) *Attorney, Agent, or Firm* — Gelu Comanescu

(57) ABSTRACT

Robotic systems and methods for the automatic guidance of medical catheters into anatomical structures during various medical procedures are disclosed. A motor controlled insertion mechanism and a motor controlled rotation mechanism are configured to combine catheter insertion and rotation such as to twist the catheter while advancing into the anatomical structure. A navigation-system determines the position in the anatomical structure of a tracking-sensor disposed on the tip of the catheter. The motion of the catheter is controlled via the motors A controller controls, via the motors, the movement of the catheter into the anatomical structure function of the position of the tracking sensor. The methods, systems and devices described herein significantly decrease X-ray exposure to both patient and doctor, minimize friction between the catheter and robotic components, reduce the size of robotic systems, reduce production costs, and reduce the duration of clinical procedures.

18 Claims, 5 Drawing Sheets

(51) Int. Cl.
  *A61B 18/14*   (2006.01)
  *A61B 17/00*   (2006.01)

(56) References Cited

U.S. PATENT DOCUMENTS

| | | |
|---|---|---|
| 9,179,979 B2 | 11/2015 | Jinno |
| 9,603,667 B2 | 3/2017 | Yang et al. |
| 10,245,112 B2 | 4/2019 | Kottenstette et al. |
| 10,271,910 B2 | 4/2019 | Wenderow et al. |
| 10,299,867 B2 | 5/2019 | Wenderow et al. |
| 10,342,953 B2 | 7/2019 | Wenderow et al. |
| 2003/0088179 A1* | 5/2003 | Seeley ................ A61B 6/4441 600/424 |
| 2005/0010237 A1* | 1/2005 | Niazi ................ A61B 17/3421 606/129 |
| 2008/0281181 A1 | 11/2008 | Manzione |
| 2009/0138025 A1 | 5/2009 | Stahler |
| 2009/0248042 A1* | 10/2009 | Kirschenman ......... A61B 34/71 606/130 |
| 2016/0279394 A1 | 9/2016 | Moll |
| 2017/0151027 A1* | 6/2017 | Walker .................. A61B 34/30 |
| 2017/0367776 A1 | 12/2017 | Kwok |

\* cited by examiner

SYSTEMS AND METHODS FOR AUTOMATIC GUIDANCE OF MEDICAL CATHETERS AND ENDOSCOPES

CROSS REFERENCE TO RELATED APPLICATION

This application claims priority from and the benefit of U.S. Provisional Patent Application No. 62/687,746 filed on Jun. 20, 2018 and titled "ROBOTIC SYSTEM FOR AUTOMATIC GUIDANCE OF MEDICAL CATHETERS", which is hereby incorporated by reference for all purposes as if fully set forth herein.

BACKGROUND OF INVENTION

I. Field of the Invention

Exemplary embodiments of the present invention relate to systems for guidance of medical catheters and endoscopes and to methods of using the same.

II. Discussion of the Background

Medical interventions such as endovascular procedures, lung nodules biopsy, or any other procedures requiring the insertion of a catheter inside the human body demand using CT and fluoroscopy imaging guidance that will result in a long and potentially damaging X-ray exposure of the patient and the doctor. Lung cancer is the most common cancer globally with over 2 million new cases diagnosed every year. Fortunately, if caught early, the likelihood of survival is greatly improved. If diagnosed in Stage I, survival rates are >75% over 5 years, vs. just 1% if diagnosed in Stage IV. Early diagnosis requires finding and sampling (biopsy) small, peripheral nodules that are located in the substance of the lung and predominately outside small airways. Currently, patients undergo radiologic imaging of the lungs that identifies a suspicious nodule, often prompting diagnostic procedures. In bronchoscopy a video camera is inserted into the airway, but due to large size it cannot reach the malignant lung nodules in the small airways. To biopsy them, the Bronchoscopist has to advance a sharp biopsy needle or forceps blindly through the lung tissue in the approximate direction of the nodule. To improve the accuracy of the procedure real time x-ray (fluoroscopy) is performed, exposing the patient and physician to harmful radiation.

Computer assisted surgery and medical robotics present viable solutions but are not optimal at present. Some of the limitations are high cost, limited use due to the complexity of the procedures, targeting accuracy, large size of the system, lack of suitable instruments for specific procedures, increased friction between catheter like instruments and robotic parts.

The application herein addresses the need for performing precise and efficient medical interventions (such as inserting catheters, probes and endoscopes) while minimizing the exposure to X-rays and other harmful radiation.

The above information disclosed in this Background section is only for enhancement of understanding of the background of the invention and therefore it may contain information that does not form any part of the prior art.

SUMMARY OF THE INVENTION

Exemplary embodiments of the present invention provide a robotic system with navigation for automatic inserting and guiding medical catheters trough the vascular system, pulmonary airways, etc. The robotic system may be used for guiding of medical catheters, endoscopes and similar rigid or flexible surgical instruments (e.g. guidewires, radio or cryo-ablation catheters, biopsy needles, forceps, clamps, sutures, scissors, scalpels, etc.).

In an exemplary embodiment it is disclosed a robotic system for guiding catheters into an anatomical structure of a patient. The robotic system may include a catheter configured to be inserted in the anatomical structure or to be directed to the close proximity of the anatomical structure. The catheter may include a tracking-sensor close to catheter tip. The robotic-system may further include a robotic catheter-driver which may include a catheter-insertion-mechanism configured to drive, via a motor, the catheter into or close to the anatomical structure. The robotic system may further include a catheter-rotation-mechanism configured to rotate the entire catheter-insertion-mechanism, via a motor, thereby rotating the catheter into or in the close proximity of the anatomical structure. The robotic system may further include a driver-controller configured to control, via the motors, the motion of the catheter. The robotic system may further include a navigation-system configured to determine the position of the tracking-sensor with respect to one or more tracking-markers and a computer configured to receive information from the navigation-system and to calculate the position of the tracking-sensor in the anatomical structure. The driver-controller may be configured to receive information from the computer regarding moving the catheter and to control the motion of the catheter into the anatomical structure by controlling the motors.

In an exemplary embodiment it is disclosed a method for performing a medical procedure on an anatomical structure of a patient by using the robotic-system. The method may include attaching on the body of the patient a tracking marker of a navigation system and performing a CT/MRI imaging on the patient such as to capture the anatomical structure and the marker. The method may further include rendering a 3D model of the anatomical structure in a reference frame attached to the marker and loading said 3D model on the computer and calculating, via the computer, an access-path (e.g. along an artery, trachea, esophagus) and a target point on the 3D model of the anatomical structure. The method may further include inserting a catheter at a point on the body corresponding to an entry point of the access-path and guiding the catheter on the access-path towards target point.

In another exemplary embodiment it is disclosed a robotic driver configured to drive a flexible instrument. The robotic driver may further include an insertion-mechanism configured to drive the flexible instrument, via a motor, into an anatomical structure. The robotic driver may further include a rotation-mechanism configured to rotate, via a motor, the entire insertion-mechanism thereby rotating the flexible instrument into the anatomical structure. The robotic driver may further include a driver-controller configured to control, via the motors, the insertion and the rotation of the flexible instrument. The flexible instruments may be guidewires, radio or cryo-ablation catheters, biopsy needles, forceps, clamps, sutures, scissors, scalpels, etc.

The robotic systems disclosed herein significantly decreases X-ray exposure to both patient and doctor; minimizes the friction between catheter and robotic components; reduces the overall size of the robotic system; reduces production costs; and reduces the duration of clinical procedures.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
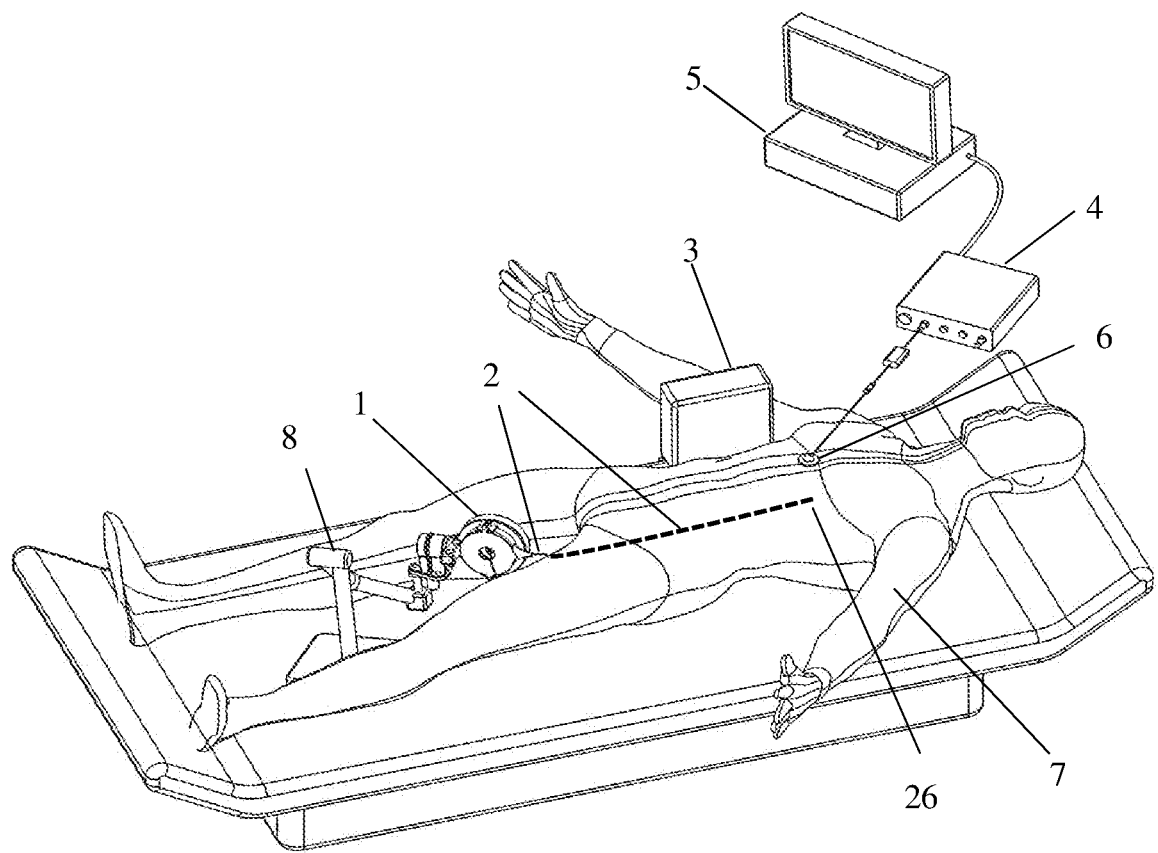
FIG. 1 shows an exemplary embodiment of a robotic system for guidance of medical catheters, bronchoscopes and endoscopes.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

It will be understood that when an element or layer is referred to as being "on" or "connected to" another element or layer, it can be directly on or directly connected to the other element or layer, or intervening elements or layers may be present. In contrast, when an element or layer is referred to as being "directly on" or "directly connected to" another element or layer, there are no intervening elements or layers present. It will be understood that for the purposes of this disclosure, "at least one of X, Y, and Z" can be construed as X only, Y only, Z only, or any combination of two or more items X, Y, and Z (e.g., XYZ, XY, YY, YZ, ZZ).

The application discloses a robotic-system for guiding catheters as described with reference to FIGS. 1-5. The robotic-system may include: a robotic catheter-driver (1); a catheter (2); a tracking-system; and a computer-system.

The robotic catheter-driver (1) may be a 2-degree-of-freedom (2DOF) robot configured to automatically insert a catheter (2) into an anatomical structure of a patient (7) in order to perform one or more medical procedures on the patient.

The catheter (2) may include one or more lumens and a "pre-bend tip" enabling the guiding of the catheter (2) through the anatomical structure. The catheter (2) may include an electromagnetic tracking sensor disposed close to the tip of the catheter and a wire (25). The electromagnetic-tracking-sensors disposed close to the tip may be referred hereinafter as tip-sensor (26). The tip-sensor may be connected to the wire (25) which may be running along the catheter and may connect the tip-sensor to the tracking-system. The catheter may be any of the commercially available catheter systems, such as Aurora SDOF Flex Tube, made by Northern Digital Inc, (Waterloo, Ontario, Canada). The catheter-system may further include a guidewire (e.g. Edge™ locatable wire, Medtronic, Minneapolis Minn., USA) with an EM tracking sensor disposed near the tip (e.g. Aurora SDOF sensor, Northern Digital Inc, Waterloo, Ontario, Canada). The catheter (2) may further include a camera, a probe, guidewires, sensors, guidewires, multiple lumens, other catheters, flexible medical instruments of tubular shape, guidewires, radio or cryo-ablation catheters, biopsy needles, forceps, clamps, sutures, scissors, scalpels, etc. The skilled artisan would understand that the devices herein are not limited by the types of catheters used and that many types of catheters can be used.

The tracking-system is configured to determine the position of the tip-sensor (26) disposed on the tip of the catheter. The tracking system may be an electromagnetic tracking system which may include a magnetic field generator (3), a main unit (4), a computer (5), one or more electromagnetic tracking sensors (6) disposed on the patient (7), and an arm (8) for supporting the robotic-catheter-driver (1). The electromagnetic tracking sensor (6) may be referred hereinafter as tracking marker (6). The tracking system may be configured to determine the position of the tip-sensor (26) with respect to a reference frame (e.g. xyz) attached to the marker (6). Commercially available navigation/tracking systems, such as AURORA (Northern Digital Inc.), may be used. The skilled artisan would understand that the methods and devices herein are not limited by the types of tracking systems and sensors used.

An operator (e.g. medical doctor) may use the robotic-system to perform one or more medical procedures. The operator may control the performance of such medical procedures via an application running on the computer-system, such as a planning and navigation software, and via a set of software implemented automatic prescriptions and/or procedures.

The robotic catheter-driver (1) configured to drive the catheter-system inside the anatomical-structure is described with reference to FIGS. 2-5. The catheter-driver (1) is configured to have a compact design and to generate two motions to the catheter: one linear and one rotational. An outside view of a robotic catheter-driver is described with reference to an exemplary embodiment shown in FIG. 2. The catheter-drive includes a wire (25) which is connected to the tip-sensor disposed on the catheter' tip and to the main unit (4) of the tracking-system. The robotic catheter-driver may include a catheter-insertion-mechanism, a catheter-rotation-mechanism, and a driver-controller, and multi-joint arm (8) for holding and positioning the driver.

Figure 2:
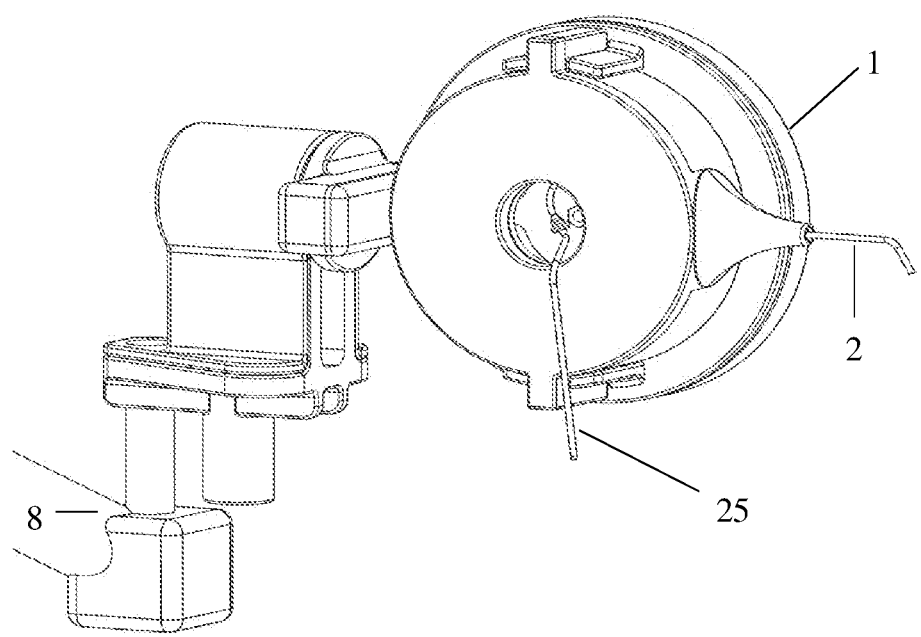
FIG. 2 shows an exemplary embodiment of the robotic catheter-driver and its mounting mechanism.
Figure 3:
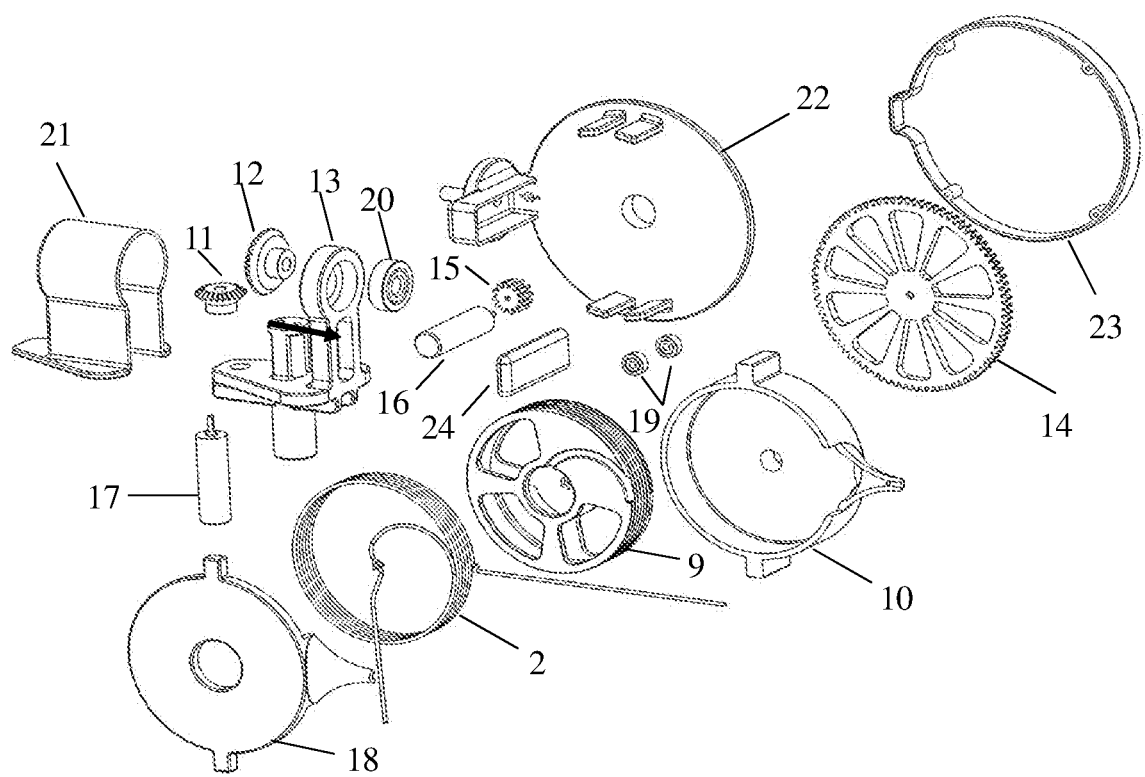
FIG. 3 shows an exemplary embodiment of the individual components of the robotic catheter-driver.

FIG. 3 shows an expanded view of the catheter-driver according to the exemplary embodiment shown in FIG. 2. The catheter-driver may include: a multi-joint arm (8) a driver-cartridge (9), a first driver-cartridge case (10), a first bevel gear (11), a second bevel gear (12), a driver support (13) for catheter rotation mechanism, a first gear (14), a second gear (15), an insertion-motor for catheter insertion movement (16), a rotation-motor for catheter rotation (17), a second driver-cartridge case (18), rotation-ball-bearings (19) for catheter rotation mechanism, insertion-ball-bearings (20) for catheter insertion mechanism, a rotation-mechanism-case (21), a driver-support (22) for catheter insertion mechanism, an insertion-mechanism-case (23), a motor-case (24) for the catheter insertion mechanism.

The catheter insertion-mechanism may be configured to drive/move the catheter (2) in a liner direction (forward & backwards) via the first-motor (16) such as to insert the catheter in the anatomical structure or to remove the catheter from the anatomical structure. For example, the insertion-mechanism may insert the catheter in the vascular system as shown in FIG. 1.

Figure 4:
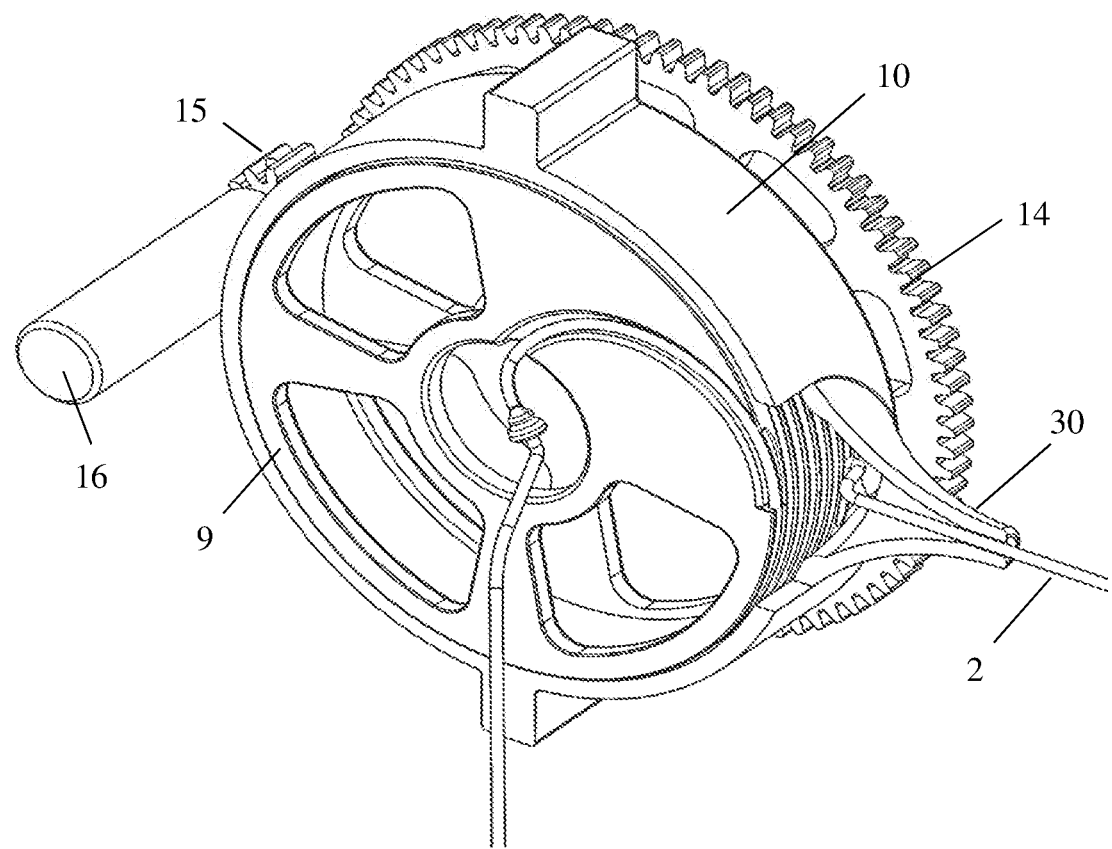
FIG. 4 shows an exemplary embodiment of the catheter mounting system of the robotic catheter driver.

FIG. 4 shows a view of the insertion-mechanism according to the exemplary embodiments described with reference to FIGS. 2 and 3. The insertion-mechanism may include the cartridge (9) on whom the catheter (2) is rolled on, as seen in FIG. 4. The catheter insertion-mechanism may further include the insertion-motor (16), gears (14) and (15), the case (10), the case (18), and the support (22). The insertion-motor (16) is configured to rotate the cartridge (9) through the gears (14) and (15), as shown in FIG. 4. When the cartridge (9) is rotated by the motor (16) through the gears (14) and (15), the catheter is unrolled and pushed through an opening (30) of the case (10), thereby inserting the catheter through the anatomical structure (e.g. patient's vascular system). Changing the rotation sense of the cartridge (9) retracts the catheter from the anatomical structure, back into the catheter-driver, and rolls the catheter on the cartridge (9).

The cartridge (9) and the catheter rolled on cartridge (9) may be encapsulated in cases (10) and (18). The cartridge (9) and the cases (10) and (18) may be mounted on the support (22). The catheter-driver is configured such that, during operation, when the catheter reaches the target in the anatomical structure (e.g. patient's vascular system), the case (18) may be opened and the catheter (2) may be detached from the cartridge (9). The insertion-mechanism may be configured such that, after case (18) is removed, the cartridge (9) may be removed from the case (10). After catheter (2) is detached from the cartridge (9), the catheter-driver (1) may be moved away from the patient, while the catheter (2) remains in the patient during the medical procedure (e.g. stenting, biopsy, etc.).

The catheter insertion-mechanism is configured such as to reduce the friction between the catheter (2), the opening (30) and other components.

Figure 5:
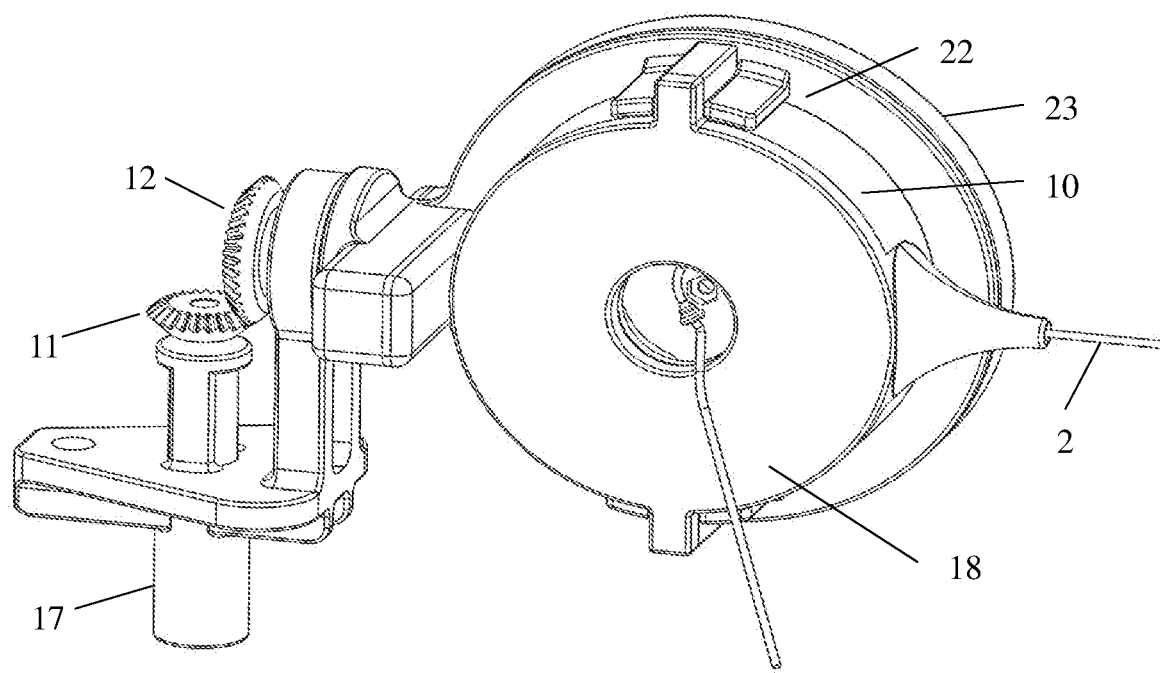
FIG. 5 shows an exemplary embodiment of the catheter driver and the coupling of the catheter cassette to the robotic catheter-driver.

The catheter rotation-mechanism is configured to provide a rotational motion to the catheter (2) around the axis of the catheter. The rotational motion is obtained using the motor (17) and the bevel gears (11) and (12), as shown in FIG. 5. The motor (17) rotates bevel gear (11); bevel gear (11) rotates bevel gear (12); bevel gear (12) rotates the entire catheter-insertion-mechanism, which in turn rotates the catheter 12 around its axis. The rotational motion is transferred to the catheter by rotating the entire catheter-insertion-mechanism, including the support (22), the gears (14) and (15), the motor (16), parts enclosed in the cases (10) and (18), the cartridge (9) and catheter (2) rolled on the cartridge (9).

The catheter insertion-mechanism and the catheter rotation-mechanism are configured to work together such as to provide the desired movement to the catheter (e.g. combination of translational/insertion and rotational movements) .The rotational motion is configured to twist the catheter while it is advanced inside the anatomical structure (e.g. inside the vascular system) such as to select a particular branch when the tip of the catheter reaches an intersection of the anatomical structure, such as an intersection in the vascular tree.

The driver-controller is configured to drive and control the movement of the catheter into the anatomical-structure by controlling the motors driving the catheters. The driver-controller is configured to receive information from the computer system and, based on this information, to control the motors, thereby controlling the movement of the catheter-system. The motors may be controlled via an IEEE/LabVIEW interface (provide some standard/system name). The controller may be configured to control other components and functionalities of the catheters, such as: sensors, probes, cameras, etc.

The multi-joint arm (8) is configured to hold and position the catheter-driver. The multi-joint arm may include a mechanism to attach to the base or the side of the operating table, and a mechanism to fix the robotic catheter-driver at different angles.

The catheter (2) rolled on the cartridge (9) and enclosed in cases (10) and (18) form a cartridge-assembly, such as a cassette, which is separable from the rest of the catheter-driver (1). The cartridge-assembly may be loaded into the catheter-driver (i.e. a catheter driver without the cartridge-assembly) by mounting the cartridge-assembly on the support (22). The cartridge-assembly may be removed, as a whole, from the catheter-driver. The cartridge-assembly may be configured to be single-use component and may come pre-assembled and sterilized.

The cartridge (9) may hold the catheter coiled on the cartridge and may push forward or pull backward the catheter when the cartridge is rotated. The cartridge may include a spiral channel and the catheter may be coiled on the spiral channel (e.g. by laying on the spiral channel). Thus, when the cartridge is rotated, the catheter is pushed forward or pulled backward, advancing or retracting. The cartridge design (e.g. including the spiral channel) minimize the friction between the catheter (2) and the parts of the catheter-driver, such as at the opening (30), by imposing a rolling movement to advance or retract the catheter.

In another exemplary embodiment, it is disclosed a flexible-instruments-driver having a configuration similar to the one described above with respect to the catheter-driver (1) which can be used to drive one or more of the following: a guidewire, a catheter, an endoscope, a probe, etc. Thus, the flexible-instruments-driver may include essentially the same elements as the robotic catheter-driver (1) and may have the same functionalities but may be configured to drive a guidewire or other flexible instruments. The cartridge of cylindrical shape may hold the flexible instrument (e.g. catheter, guidewire, etc.) coiled on the cartridge (e.g. in a spiral channel) and may push forward or pull backward the flexible instrument when the cartridge is rotated. The cartridge may include a spiral channel and the flexible instrument may be coiled on the spiral channel (e.g. by laying on the spiral channel). Thus, when the cartridge is rotated, the flexible instrument is pushed forward or pulled backward, advancing or retracting. The cartridge design (e.g. including the spiral channel) minimize the friction between the flexible instrument and the driver parts by imposing a rolling movement to advance or retract the instrument.

The robotic system may be used for guiding of medical catheters, endoscopes and similar rigid or flexible surgical instruments, such as: guidewires, radio or cryo-ablation catheters, biopsy needles, forceps, clamps, sutures, scissors, scalpels, etc.

The computer system may include a computer configured to receive/send information to the EM tracking-system, the controller of the catheter-driver, Computer Tomography (CT) machines, Magnetic Resonance Imaging (MRI) machines, Ultrasound (US) machines, etc. The computer system may include input devices, such as keyboard, mouse, joysticks, enabling operators to control the robotic-system.

The computer system may include a plurality of software modules, such as: a medical procedure planning module, a navigation module, a user interface module, an imaging module for processing and viewing CT/MRI/US images etc.

The medical procedure planning module and the navigation module may be implemented via the iMTCEH software packages in conjunction with CustusX or other available freeware libraries (for example for additional algorithms and mathematical formulas to improve navigation precision). The planning module may be used by the surgeon to identify the target on one or more images corresponding to the anatomical structure (e.g. the patient's CT scan before the procedure), and a navigation module used by the controller to drive the catheter.

The imaging module may be configured to receive one or more CT/MRI images corresponding to an anatomical structure of the patient and to one or more tracking markers disposed on patient's body. The imaging module may include software configured to fuse one or more CT/MRI/US images into one fused image. The imaging module may include software configured to create a 3D map of anatomical structure, wherein the position of the mapped points are expressed with reference to a coordinate system attached to the tracking markers.

The user interface module (navigation interface) enables operators to control the robotic-system via input devices, such as keyboard, mouse, joystick, etc.

The following describes how all elements work together to provide a functional robotic system. As described above, the robotic-system includes a plurality of devices and systems working together to achieve the desired functionalities. The functionalities of the robotic-system are implemented via software controlling individual components of the robotic-system, the interaction between components, the interaction with operators, and the interaction with the anatomical structure. The following section describe a robotic-system configured to run a plurality of medical-procedures.

In an exemplary embodiment, the functioning of the robotic-system is described with reference to a cardiac catheterization procedure performed by an operator (e.g. a cardiac or a vascular surgeon). In this context, the operator will first identify an anatomical structure within the cardiovascular system (heart or major blood vessels) as the target for vascular stent placement or angioplasty procedure. The patient's anatomy in the area of interest (i.e. the abdominal and thoracic regions) will be reconstructed from the patient's CT scan. Prior to the procedure, a CT scan of the patient is acquired after an electromagnetic tracking sensor, such as marker (6), is placed on patient chest. The patient is moved in the endovascular procedure room, keeping the sensor (6) on his chest and the electromagnetic tracking system (ETS) is placed near patient and connected to the computer. The surgeon is choosing the catheter insertion and target on CT scans and the software's planning module will automatically compute a path from the insertion point to the target. A planning procedure will allow the operator to visualize the pathway from an entry point (i.e. the femoral artery or vein) to the target (i.e. a lesion or atherosclerotic plaque in the abdominal or thoracic aorta or the heart).

The pre-assembled cartridge-assembly is loaded in the catheter-driver (1) by mounting on the support (22). The catheter-driver (1) is fixed on the patient table, and the multi-joint arm (8) is used to adjust the catheter-driver in proper position for intravascular insertion. The electric wire (25) from the catheter is connected to the ETS.

Starting from the catheter (2) being completely rolled on the cartridge (9) the operator may manually unroll the catheter (2) off the cartridge (9) such as to allow the surgeon to insert the catheter tip in the patient vascular system as in a classic procedure. The software of the robotic system performs an automatic registration procedure between CT data and the patient using the tracking marker (6). The registration is performed by finding a position of the reference sensor in the virtual 3D space similar to the position of the real sensor in the real space.

The inventors have conceived a robotic system which, unlike the current state of the art systems, allows the operator to choose one of three different use modes: manually, semi automatically and fully automatically. During any these modes, the operator uses the Electromagnetic (EM) navigation procedure in order to advance the medical instrument (e.g. a catheter equipped with a guidewire, a forceps or other interventional instrument) to the desired target. Currently the vascular medical robots are only manually directed via a joystick (i.e. CorePath GRX, Corindus Vascular Robotics, Waltham, Mass., USA). While manual control reduces or eliminates the operator's exposure to harmful radiation, it does not do so for the patient. In contrast, the semi-automatic and fully automatic modes disclosed herein almost completely remove the need to expose either the patient or the operator to harmful radiation such as fluoroscopy. The robotic systems disclosed in this application allows for the medical instrument to be directed to the target and to perform biopsy or other medical procedure more accurately and precisely while the catheter is maintained in place.

The tracking tip-sensor (26) and the ETS provides continuously to the software the position of the catheter's tip relative to the patient. As a result, the robotic system can determine, virtually at all times, if the catheter tip is on the right path.

Using the ETS and the software navigation module, the robotic-system can precisely reach a target, without the need of X-ray scanning during catheter insertion, by moving the catheter on the planned path. When encountering a branch bifurcation of the anatomical structure (e.g. bifurcation of blood vessels) the robotic-system may select a specific vessel branch by a combination of rotating, inserting and retracting the catheter until the pre-bended tip aligns into the right direction and advances on the desired branch.

After the target is reached and confirmed, the case (18) may be opened and the catheter may be uncoupled from the catheter-driver. The tip-sensor can be retracted from the working channel of the catheter and another instrument can be inserted through the catheter, such as biopsy needles for standard biopsy collection or a endomiscroscopy probe for acquiring imaging data.

In another exemplary embodiment, the robotic system may be used for navigating to peripheral lung lesions for early lung cancer diagnosis and treatment. In this context, the anatomical target is represented by small (<1 mm) suspicious lesions located at the periphery of the lung where the normal bronchoscopes cannot reach. Similar to the cardiovascular application, after the patient's anatomy is reconstructed from the diagnostic CT scan, an entry point (i.e. the trachea or main pulmonary airway) and a target (i.e. the suspicious lung lesion detected during the CT examination) will be defined in the virtual 3D model of the patient's anatomy. The robotic system will guide a catheter and various medical instruments from the entry point to the target under the guidance of the navigation software.

Several software implemented methods for operating the robotic system are described hereinafter.

Method-1 (Automatic Mode):

A method for performing a medical procedure on an anatomical-structure of a patient by using the robotic-system above is disclosed. The method may include the attaching on the patient body a tracking marker of the navigation system and performing a CT/MRI imaging on the patient such as to capture the anatomical structure and the marker. The method may further include the rendering of a 3D model of the anatomical-structure (e.g. in a reference frame attached to the marker), followed by loading said 3D model on the computer.

The method may further include calculating, via the computer, an access-path (e.g. via an artery, trachea, esophagus, etc.) and a target point on the 3D model of the anatomical-structure. The method may further include inserting a catheter at a point on the body corresponding to an entry point of the access-path and guiding the catheter on the access-path towards target point.

The guiding of the catheter towards the target point may include the steps described hereinafter. Step-1 includes the receiving, via the navigation-system, information from the tracking-tip-sensor and calculating a current position for tracking-tip-sensor on the access path. Step-2 includes calculating a desired path-section (e.g. a 2 mm long path) along which to move the catheter tip from the current position towards the target point. Step-3 includes calculating a set of motor motions, for the insertion-motor and the rotation-motor, corresponding to moving the catheter on the desired path-section. Step-4 includes sending to the motors, via the driver-controller, a set of signals corresponding to the set of motor motions. The above steps are then the repeated iteratively until the tip of the catheter reaches the target point.

Once the tip of the catheter has reached the target point, the catheter-driver may be disconnected from the catheter and the tracking sensor may be removed.

Method-2 (Semi-Automatic Mode):

A method for performing a medical procedure on an anatomical-structure of a patient by using the robotic-system above is disclosed. The method may include the attaching on the patient body a tracking marker of the navigation system and performing a CT/MRI imaging on the patient such as to capture the anatomical structure and the marker. The method may further include the rendering of a 3D model of the anatomical-structure in a reference frame attached to the marker, followed by loading said 3D model on the computer.

The method may further include calculating, via the computer, an access-path (e.g. via an artery, trachea, esophagus, etc.) and a target point on the 3D model of the anatomical-structure. The method may further include inserting a catheter at a point on the body corresponding to an entry point of the access-path and guiding the catheter on the access-path towards target point.

The guiding of the catheter towards the target point may include the steps hereinafter. Step-1 includes the receiving, via the navigation-system, information from the tracking-tip-sensor and calculating a current position of the tracking-tip-sensor on the access path. Step-2 includes defining a desired path-section (e.g. a 2 mm long path) along which to move the catheter from the current position towards the target point. Step-3 may include directing the driver's motors via a computer interface. The computer interface, which is displayed on a monitor, may include up/down arrows for advancing/retracting the catheter and left/right arrows for rotating the catheter left/right. Alternatively, step-3 may include directing the driver's motors via a joystick enabling the operator to manually control the moving of the catheter on the desired path-section. The above steps are then repeated iteratively until the tip of the catheter reaches the target point.

Once the tip of the catheter has reached the target point, the catheter-driver may be disconnected from the catheter and the tracking sensor may be removed.

Method-3 (manual mode, using regular fluoroscopy or a video camera of the bronchoscope/endoscope):

A method for performing a medical procedure on an anatomical-structure of a patient by using the robotic-system above is disclosed. The method may include the attaching on the patient body a tracking marker of the navigation system and performing a CT/MRI imaging on the patient such as to capture the anatomical structure and the marker. The method may further include the rendering of a 3D model of the anatomical-structure in a reference frame attached to the marker, followed by loading said 3D model on the computer.

The method may further include calculating, via the computer, an access-path (e.g. via an artery, trachea, esophagus, etc.) and a target point on the 3D model of the anatomical-structure. The method may further include inserting a catheter at a point on the body corresponding to an entry point of the access-path and guiding the catheter on the access-path towards target point.

The guiding of the catheter towards the target point may include steps 1 and 2 described hereinafter. Step-1 includes receiving, via the traditional imaging modality (i.e. fluoroscopy or the bronchoscope/endoscope video camera) information of the current position of the catheter. Step-2 may include directing the driver's motors via a computer interface. The computer interface, which is displayed on a monitor, may include up/down arrows for advancing/retracting the catheter and left/right arrows for rotating the catheter left/right. Alternatively, step-2 may include directing the driver's motors via a joystick enabling the operator to manually control the moving of the catheter on the desired path-section. The above steps are then repeated iteratively until the tip of the catheter reaches the target point.

Once the tip of the catheter has reached the target point, the catheter-driver may be disconnected from the catheter and the tracking sensor may be removed.

The robotic systems and methods described in this application can be used and customized for a plurality of medical procedures and applications. Different embodiments of the robotic-system may be used for different medical procedures. The embodiments of the robotic systems may include: robotic-systems for automatic guidance of biopsy catheters to peripheral pulmonary airway targets; robotic-systems for guiding catheters during cardiac catheterization; robotic-systems for guiding catheters during Esophagogastroduodenoscopy; robotic-system for endovascular procedures; robotic-system for guiding colonoscopes or colonoscope based medical instruments during a colonoscopy, etc. Different embodiments may include different technical features (e.g. different catheters, cameras, ultrasound, LEDs, tips, instruments, software, etc.) specific for various procedures, such as cardiac catheterization, GI endoscopy, pulmonary endoscopy, colonoscopy, or any procedure for biopsy collection inside anatomical targets.

The skilled artisan will understand that the robotic-systems disclosed herein could include various types of components implementing many types of functionalities. For examples, various types of guidewires and catheters could be used, such as the ones specifically designed for: endoscopy, bronchoscopy, colonoscopy, cardiac catheterization.

Various types of endoscopes could be used, for different applications such as for: gastrointestinal tract (esophagus, stomach, and duodenum (esophagogastroduodenoscopy), small intestine (enteroscope), large intestine/colon (colonoscope, sigmoidoscope), bile duct, rectum (rectoscope), and anus (anoscope); respiratory tract: nose (rhinoscope), lower respiratory tract (bronchoscope); ear: otoscope; urinary tract: cystoscope; female reproductive tract (gynoscope): cervix (colposcope), uterus (hysteroscope), fallopian tubes (falloposcope); through a small incision: abdominal or pelvic cavity (laparoscope), interior of a joint (arthroscope), organs of the chest (thoracoscope and mediastinoscope).

Various types of catheter tips could be used, such as: straight, bend or partially bend tips. Various types of probes/sensors/electrodes could be used, such as: force sensors, cameras, LEDs, electrodes, piezo-electric sensors, fluid or gas pressure sensors.

The robotic systems disclosed herein significantly decreases X-ray exposure to both patient and doctor; minimizes the friction between catheter and robotic components; reduces the overall size of the robotic system; reduces production costs; and reduces the duration of clinical procedures. The robotic-system and methods provides patients with a "one-stop" diagnostic and treatment procedure as opposed to a procedure requiring a combination of procedures, such as a combination of bronchoscopy for diagnosis (i.e. via tissue biopsy) and open or laparoscopic surgery for treatment (i.e. tissue removal or ablation) as it is the currently performed. The robotic-system may include special instruments manipulated by smart robotic system, EM tracking, software controlling robot movements, and laparoscopic instruments with optical and EM tracking capabilities.

The inventors have developed prototypes of the robotic-system disclosed in this application (also referred as Computer Guided Surgical Navigation system) performing: a 3D anatomy model from CT or MRI scans, a surgical procedure planning for difficult anatomy and small peripheral targets, simultaneous electromagnetic (EM) and optical navigation for single or multiple instrument guidance to improve accuracy.

The inventors have also developed functional prototypes of a small profile robotic-system (called the EndoRo™) for manual to fully automatic remote operation of multiple medical instruments under EM, optical or traditional imaging (fluoroscopy) guidance. As compared to existing medical robotic systems, the benefits of the EndoRo™ system include: lower cost (low production and operation cost and lower training costs), smaller size (reduced OR space and a single arm), higher use (intuitive, adaptable to many tools/procedures), many suitable tools (i.e. tissue biopsy, tissue markers, forceps).

Although only a few embodiments have been described in detail above, those skilled in the art can recognize that many variations from the described embodiments are possible without departing from the spirit of the invention.

Embodiments of the invention are described herein with reference to figures and illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

The systems disclosed herein may include alternate or additional devices which could be added based on procedural needs. It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalent.

The invention claimed is:

1. A robotic-system for guiding catheters into an anatomical-structure of a patient, the robotic-system comprising:
    a catheter configured to be inserted in an anatomical-structure or to be directed to the close proximity of an anatomical structure, the catheter comprising a tracking-sensor close to catheter tip;
    a robotic catheter-driver comprising:
        a catheter-insertion-mechanism comprising an insertion-motor configured to drive the catheter into or close to the anatomical structure;
        a catheter-rotation-mechanism comprising a rotation-motor configured to rotate the entire catheter-insertion-mechanism, thereby being configured to rotate the catheter into the anatomical structure;
        a driver-controller configured to control, via the insertion-motor and the rotation-motor, the motion of the catheter;
    a navigation-system configured to determine the position of the tracking-sensor with respect to one or more tracking-markers; and
    a computer configured to receive information from the navigation-system and to calculate the position of the tracking-sensor in the anatomical structure;
    wherein the driver-controller is configured to receive information from the computer regarding moving the catheter and to control the motion of the catheters into the anatomical structure by controlling the insertion-motor and the rotation-motor.

2. The robotic-system of claim 1, wherein the insertion-mechanism comprises:
    a cylindrical cartridge on which the catheter is partially rolled on;
    wherein by rotating the cylindrical cartridge in a first direction the catheter is rolled off the cylindrical cartridge and pushed towards and into the anatomical structure;
    wherein by rotating the cylindrical cartridge into a second direction the catheter is rolled on the cylindrical cartridge and retracted from or away of the anatomical structure.

3. The robotic-system of claim 2, wherein the robotic catheter-driver comprises a cartridge-assembly comprising the insertion-mechanism and the catheter, wherein the cartridge-assembly is separable from the catheter-driver.

4. The robotic-system of claim 3, wherein the cartridge-assembly is configured to be a single use component which comes preassembled and sterilized.

5. The robotic-system of claim 2, wherein the cylindrical cartridge includes a spiral channel grooved on the surface of the cylindrical cartridge and the catheter may be rolled on the cartridge by following the spiral channel.

6. The robotic-system of claim 1, wherein the catheter tip is a pre-bended tip such that upon the tip of the catheter reaching a bifurcation inside the anatomical structure, the pre-bended tip enables an operator to select a branch along which to advance.

7. The robotic-system of claim 1, wherein the insertion-motor and rotation-motors are configured to simultaneously insert and rotate the catheter, thereby being configured to twist the catheter while advancing into the anatomical structure.

8. The robotic-system of claim 1, wherein the computer comprises one or more software modules comprising:
- a user interface module;
- an imaging module configured to receive a 3D model of the anatomical-structure, the 3D model being obtained by performing a CT scan or other imaging procedures on the patient; and
- a navigation and planning module configured to calculate on the 3D model an access-path towards a target point.

9. The robotic-system of claim 8, wherein the computer enables an operator to use the robotic-system in one or more operation modes for guiding the catheter on the access-path towards the target point.

10. The robotic-system of claim 9, wherein the one or more operation modes comprise an automatic mode further comprising:
- step-A1 of receiving, via the navigation-system, information from the tracking-sensor and calculating a current position for the tracking-sensor on the access path;
- step-A2 of calculating a desired path-section along which to move the catheter from the current position towards the target point;
- step-A3 of calculating a set of motor motions, for the driver's motors, corresponding to moving the catheter on the desired path-section;
- step-A4 of sending to the insertion-motor and the rotation-motor, via the driver-controller, a set of signals corresponding to the set of motor motions; and
- iteratively repeating step-A1, step-A2, step-A3 and step-A4 until the tip of the catheter reaches the target point.

11. The robotic-system of claim 10, wherein the one or more operation modes further comprise a semi-automatic mode, the semi-automatic mode further comprising:
- step-B1 of receiving, via the navigation-system, information from the tracking-sensor and calculating a current position for the tracking-sensor on the access path;
- step-B2 of calculating a desired path-section along which to move the catheter from the current position towards the target point;
- step-B3 of receiving input from an operator, via an user interface or a joystick, the input directing the insertion-motor and the rotation-motor such as to move the catheter on the desired path-section; and
- iteratively repeating step-B1, step-B2 and step-B3 until the tip of the catheter reaches the target point.

12. The robotic-system of claim 11, wherein the computer interface is displayed on a monitor, and wherein the interface comprises:
- up arrows for advancing the catheter into the anatomical structure;
- down arrows for retracting the catheter from the anatomical structure;
- left arrows for rotating the catheter to the left; and
- right arrows for rotating the catheter to the right.

13. The robotic-system of claim 11, wherein the operation modes further comprise a manual-mode, the manual mode further comprising:
- step-C1 of receiving, via a regular imaging modality, information regarding the position of the catheter tip inside the anatomical structure;
- step-C2 of receiving input from an operator, via an user interface or a joystick, the input directing the insertion-motor and the rotation-motor such as to move the catheter on the desired path-section; and
- iteratively repeating step-C1 and step-C2 until the catheter tip reaches the target point.

14. A method for performing a medical procedure on an anatomical-structure of a patient by using the robotic-system at claim-1, the method comprising:
- attaching on the body of the patient a tracking marker of the navigation system and performing a CT/MRI imaging on the patient such as to capture the anatomical structure and the marker;
- rendering a 3D model of the anatomical-structure in a reference frame attached to the marker and loading said 3D model on the computer;
- calculating, via the computer, an access-path and a target point on the 3D model of the anatomical-structure;
- inserting a catheter at a point on the body corresponding to an entry point of the access-path;
- guiding the catheter on the access-path towards target point, wherein the guiding comprises:
  - step-1: receiving, via the navigation-system, information from the tracking-sensor and calculating a current position for tracking-sensor on the access path;
  - step-2: calculating a desired path-section along which to move the catheter from the current position towards the target point;
  - step-3: calculating a set of motor motions, for the driver's motors, corresponding to moving the catheter on the desired path-section;
  - step-4: sending to the motors, via the driver-controller, a set of signals corresponding to the set of motor motions; and
  - iteratively repeating step-1, step-2, step-3 and step-4 until the tip of the catheter reaches the target point.

15. The method of claim 14, further comprising the disconnecting the catheter-driver from the catheter and performing one or more of the following:
- inserting an endomicroscopy probe in the catheter so as to reach the target point and acquiring imaging data; and
- inserting in the catheter an instrument for performing biopsy and performing the biopsy.

16. A robotic driver configured to drive a flexible instrument, the robotic driver comprising:
- an insertion-mechanism comprising an insertion-motor configured to drive the flexible instrument into an anatomical structure;
- a rotation-mechanism comprising a rotation-motor configured to rotate the entire insertion-mechanism thereby rotating the flexible instrument into the anatomical structure;
- a driver-controller configured to control, via the insertion-motor and the rotation-motor, the insertion and the rotation of the flexible instrument.

17. The robotic driver of claim 16, wherein the insertion-mechanism comprises:
- a cylindrical cartridge on which the flexible instrument is partially rolled on;
- wherein by rotating the cylindrical cartridge in a first direction the flexible instrument is rolled off the cylindrical cartridge and pushed towards and into the anatomical structure;
- wherein by rotating the cylindrical cartridge into a second direction the flexible instrument is rolled on the cylindrical cartridge and retracted from or away of the anatomical structure.

18. The robotic driver of claim 17, wherein the driver comprises a cartridge-assembly comprising the insertion-mechanism and the flexible instrument and wherein the cartridge-assembly is separable from the catheter-driver.

\* \* \* \* \*